United States Patent
Lind et al.

(10) Patent No.: US 9,623,406 B2
(45) Date of Patent: Apr. 18, 2017

(54) ELECTRONIC PIPETTE (71) Applicant: Thermo Fisher Scientific Oy, Vantaa (FI)

(72) Inventors: Mikael Lind, Helsinki (FI); Arto Pekkanen, Helsinki (FI)

(73) Assignee: Thermo Fisher Scientific Oy, Vantaa (FI)

( * ) Notice: Subject to any disclaimer, the term of this patent is extended or adjusted under 35 U.S.C. 154(b) by 0 days.

(21) Appl. No.: 15/102,692

(22) PCT Filed: Dec. 10, 2014

(86) PCT No.: PCT/FI2014/050975
§ 371 (c)(1),
(2) Date: Jun. 8, 2016

(87) PCT Pub. No.: WO2015/092126
PCT Pub. Date: Jun. 25, 2015

(65) Prior Publication Data
US 2016/0310937 A1 Oct. 27, 2016

(30) Foreign Application Priority Data
Dec. 18, 2013 (FI) .................................. 20136283

(51) Int. Cl.
*B01L 3/02* (2006.01)
*G01N 35/10* (2006.01)
(Continued)

(52) U.S. Cl.
CPC ............ *B01L 3/0237* (2013.01); *B01L 3/021* (2013.01); *B01L 3/0227* (2013.01);
(Continued)

(58) Field of Classification Search
CPC ...... B01L 3/0217; B01L 3/0237; B01L 3/021; B01L 3/0224; B01L 9/54; G01F 11/029;
(Continued)

(56) References Cited

U.S. PATENT DOCUMENTS 4,896,270 A * 1/1990 Kalmakis .............. B01L 3/0227
422/562
5,187,990 A 2/1993 Magnussen et al.
(Continued)

FOREIGN PATENT DOCUMENTS

EP 0576967 A2 1/1994
WO 0161308 A1 8/2001
(Continued)

OTHER PUBLICATIONS

Finnish Patent and Registration Office, Search Report, Patent Application No. 20136283, mailed Sep. 24, 2014 (2 pages).
(Continued)

*Primary Examiner* — Jennifer Wecker
(74) *Attorney, Agent, or Firm* — Wood Herron & Evans LLP (57) ABSTRACT

A method for controlling an electronic pipette, which pipette comprises a piston actuated in a cylinder by a motor, which motor is controlled with a control system, which control system is controlled through a user interface for operating the pipette, wherein actual backlash affecting the movement of the piston of the electronic pipette is measured with a system located in the pipette, the measured backlash value is forwarded to the control system of the electronic pipette, and the movement of the piston is adjusted by the control system based on the measured backlash value.

12 Claims, 5 Drawing Sheets

(51) Int. Cl.
*G01N 35/00* (2006.01)
*G01F 11/02* (2006.01)
*G01N 35/04* (2006.01)
*B01L 9/00* (2006.01)

(52) U.S. Cl.
CPC ..... *G01F 11/029* (2013.01); *G01N 35/00594* (2013.01); *G01N 35/1011* (2013.01); *B01L 3/0217* (2013.01); *B01L 3/0224* (2013.01); *B01L 9/54* (2013.01); *B01L 2200/143* (2013.01); *B01L 2200/148* (2013.01); *B01L 2300/025* (2013.01); *B01L 2300/0627* (2013.01); *B01L 2300/0832* (2013.01); *B01L 2400/0478* (2013.01); *G01N 2035/0474* (2013.01)

(58) Field of Classification Search
CPC ........ G01N 35/1011; G01N 35/00594; G01N 2035/0474
See application file for complete search history.

(56) References Cited

U.S. PATENT DOCUMENTS

| | | | |
|---|---|---|---|
| 5,343,769 A | | 9/1994 | Suovaniemi et al. |
| 5,389,341 A | * | 2/1995 | Tuunanen ............. B01L 3/0227 422/509 |
| 5,869,774 A | * | 2/1999 | Backlund ........... G01N 35/1095 417/199.1 |
| 2003/0000965 A1 | | 1/2003 | Bach et al. |
| 2009/0000350 A1 | * | 1/2009 | Magnussen ........... B01L 3/0217 73/1.74 |
| 2013/0001242 A1 | * | 1/2013 | Hofstetter ............. B01L 3/0217 222/333 |
| 2013/0283884 A1 | | 10/2013 | Beroz et al. |
| 2013/0315780 A1 | * | 11/2013 | Cook ..................... G01N 21/66 422/52 |

FOREIGN PATENT DOCUMENTS

WO 2005079987 A1 9/2005
WO 2005079989 A1 9/2005

OTHER PUBLICATIONS

European Patent Office, International Search Report and Written Opinion of the International Searching Authority, International Application No. PCT/FI2014/050975, mailed Feb. 24, 2015 (9 pages).

\* cited by examiner

ELECTRONIC PIPETTE

CROSS-REFERENCE TO RELATED APPLICATIONS

This application is a submission under 35 U.S.C. §371 of International Application No. PCT/FI2014/050975, filed Dec. 10, 2014, which claims priority to Finnish Application No. 20136283, filed Dec. 18, 2013, the disclosures of which are hereby expressly incorporated by reference herein in their entireties.

FIELD OF THE INVENTION

The present invention relates to an electronic pipette for use in the dosage of liquids and comprising a piston movable in a cylinder for aspiration and dispensing of liquid, an electric motor for moving the piston in the cylinder, and an electronic operating system with a user interface for operating the electronic pipette.

BACKGROUND OF THE INVENTION

Pipettes used for liquid dosage in laboratories comprise a piston movable in a cylinder for aspiration of liquid into a tip container connected with the cylinder. The volume is usually adjustable. There are also electronic pipettes whose piston is actuated by means of an electric motor and a control system associated with it. However, there are also electronic pipettes whose pistons are actuated by manual force and which comprise an electronic display only. Electronic pipettes have a user interface for selection of the desired pipette function (e.g., forward or reverse pipetting), setting of the volume and for giving commands for performing operations. The user interface has the necessary switches for input of the necessary settings and performance of the functions. The user interface is connected to a display, by means of which the volume and other necessary data can be displayed. The display can also show menus allowing data input in the control system.

Examples of known electronic pipettes are disclosed in International Publication Nos. WO 2005079989 and WO 2005079987, for example.

Pipettes usually have a calibration function allowing the piston stroke or the volume indicated on the display to be set so that the dosed liquid volume equals the indicated volume with maximal accuracy. In practice, calibration comprises weighing the mass of the liquid amount dosed by the pipette with an indicated volume. The liquid is usually distilled water and the calibration is performed at room temperature (20-25° C.). Usually, weighing is repeatedly carried out and the mean value of the results of the weighing operations is calculated.

However, due to the use of pipette during its lifetime, the parts of the pipette experience mechanical wear causing play and backlash between different components of the pipette, which affect the actual volumes of liquid aspired and/or dispensed with the pipette.

U.S. Pat. No. 5,187,990 discloses an electronic pipette that automatically goes through calibration process upon either powerup or restoration of power after power loss. In the calibration process, the digital linear actuator of the pipette undergoes full extension in order to properly position the piston of the pipette in its home position prior to starting the pipetting processes. For compensating air pressure and liquid surface tension, among others, the piston of the pipette is moved for additional distance during the aspiration and/or dispensing of a volume of liquid.

SUMMARY OF THE INVENTION

According to the present invention, the actual backlash affecting the movement of a piston of an electronic pipette is measured with a system located in the pipette, the measured backlash value is forwarded to a control system of the electronic pipette, and the movement of the piston is adjusted by the control system based on the measured backlash value. This way the actual backlash, which varies from pipette to pipette, and during the lifetime of the pipette, can be properly eliminated from the functioning of an electronic pipette. The backlash directly affects the amounts of liquid aspired and dispensed with an electronic pipette, so the present invention provides for more accurate pipetted amounts of liquid.

The measurement of backlash is advantageously carried out by defining the actual position of the piston in a first position, then moving the piston a set distance to a second position, then returning the piston exactly to the first position and measuring the returning distance, and then comparing the set distance from the first position to the second position and the measured distance from the second position to the first position. The difference of these distances is the actual backlash value of the pipette.

Advantageously, the backlash is measured in both movement directions of the piston of the electronic pipette. The backlash may be different for different movement directions of the piston, so by measuring the backlash in both movement directions proper measurement value can be used for aspiration and for dispensing. Further, the measurement of backlash in both directions also allows minimizing the effect of measurement inaccuracies, such as hysteresis, for example.

When the backlash is measured in both movement directions, an average value of the measured backlash values from different movement directions is advantageously used as the measured backlash value for adjustment of the movement of the piston.

The backlash measurement may advantageously be carried out each time the electronic pipette is powered up. Thus, the correct backlash value is available for pipetting operations substantially continuously. Alternatively, the backlash measurement may be carried out only during calibration process of the pipette, since the backlash value does not generally increase significantly during normal use of the pipette.

According to the method of the present invention, the definition and positioning of a home position of the piston of the electronic pipette may advantageously be implemented with the same sensor system than the backlash measurement.

Advantageously, the backlash measurement is carried out to an electronic pipette which is a handheld entity.

A method of the present invention is advantageously carried out during repetitive pipetting, in manual pipetting or in step based pipetting.

The present invention also provides an electronic pipette, comprising a piston actuated in a cylinder by a motor, a control system for carrying out pipetting operations, and a user interface for operating the pipette, which pipette is equipped with a device for measuring actual backlash affecting the movement of the piston of the electronic pipette.

Advantageously, according to one embodiment of the present invention, the device for measuring the actual backlash of the piston comprises one or more suitable sensors or sensor systems, such as an optical fork sensor, a reflecting sensor system and/or a magnetic sensor system.

Further, the device for measuring the actual backlash of the piston may be located as a part of the fixed structure of the pipette or it may be located in the piston itself or in a part moving with the piston, or it may be located partially both at the fixed structure of the pipette and in the piston itself.

Advantageously, the electronic pipette according to one embodiment of the present invention is a handheld entity.

BRIEF DESCRIPTION OF THE DRAWINGS

An exemplifying embodiment of the present invention and its advantages are explained in greater detail below in the sense of an example and with reference to the accompanying drawings, where.

DETAILED DESCRIPTION OF THE INVENTION

Figure 1:
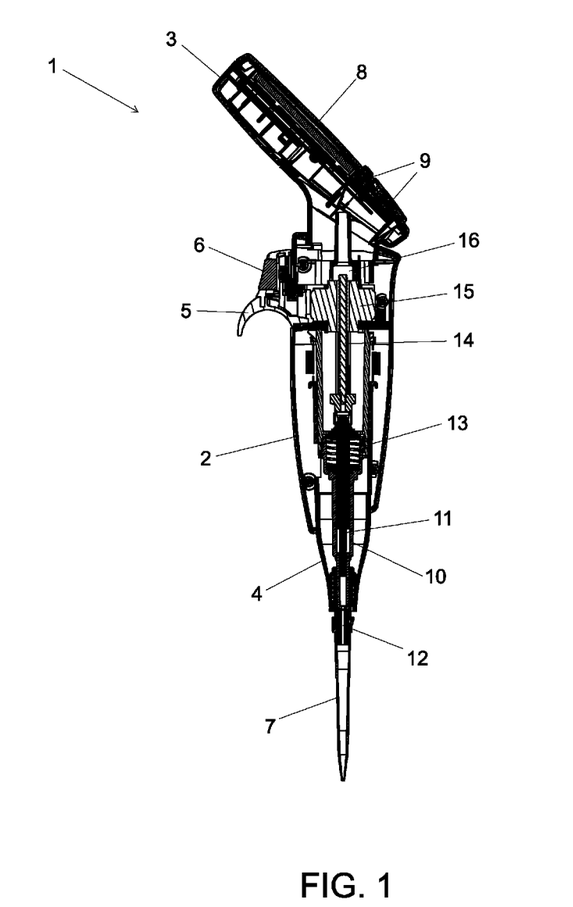
FIG. 1 shows schematically a cross-section of an electronic pipette according to the present invention.

FIG. 1 shows schematically a cross-section of an electronic pipette 1 according to one embodiment of the present invention, which is formed as a handheld entity and the body of which comprises handle portion 2, at upper end of the handle portion tilted display portion 3, and at lower end of the handle portion tip portion 4 of the pipette.

When the pipette 1 is used, it is gripped from the handle portion 2 so that middle finger of the user sets against finger support 5 at the upper part of the handle portion, which leaves index finger of the user free to operate the operating switch 6 of the pipette. To the tip portion 4 is attached detachable pipette tip 7, to which liquid is aspired and from which liquid is dispensed during the use of the pipette 1.

The outer surface of the display portion 3 of the pipette 1 is equipped with a display 8 and operation keys 9, which form the user interface of operating system of the pipette together with the operating switch 6.

Inside the body of the pipette 1, extending in the area of the handle portion 2 and the tip portion 4 of the pipette, is located a cylinder 10 and inside the cylinder piston 11 movable with respect to the cylinder, which both extend along or parallel with the central axis of the handle portion and/or tip portion of the pipette. From the lower end of the cylinder 11, extends a channel 12 at the bottom end surface of the tip portion 4 for obtaining aspiration or dispensing of liquid to and from the detachable pipette tip 7 by moving the piston 11 inside the cylinder 10. Between surfaces of the cylinder 10 and the piston 11 is located a spring member 13 extending in the length direction of the cylinder and piston for forcing the upper end of the piston against the means for moving the piston in the cylinder.

The means for moving the piston 11 comprises a linear actuator formed by a threaded rod 14, which extends along or parallel with the central axis of the handle portion 2, and an electric motor 15, which moves the threaded rod in its lengthwise direction through a threaded connection between the un-rotating threaded rod and a rotating member of the motor. By moving the threaded rod 14, the piston 11 moves accordingly inside the cylinder 10.

The pipette 1 also includes a device for measuring the actual backlash of the piston, which in this embodiment is an optical fork sensor 16 located on top of the motor 15 so that the top end of the threaded rod 14 can move between the brackets of the fork sensor. Alternatively, in the present invention the device for measuring the actual backlash of the piston may be located in the piston 11 itself or in a part moving with the piston, or it may be comprise two or more parts where at least one part is located in the piston 11 itself or in a part moving together with the piston and at least one part is located at other fixed parts of the pipette.

In the embodiment of FIG. 1, the movement of the threaded rod 14, and thus the motion of the piston 11, is controlled as step based movement. Thus, the backlash affecting the piston can be measured so, that first the threaded rod 14 is moved to a starting position by moving it upwards until the light path between the brackets of the optical fork sensor 16 is cut for the first time. From this starting position, the threaded rod 14 is moved upwards for a set amount of steps, and then downwards until unobstructed light path is obtained again in the optical fork sensor. The difference between the set amount of steps upwards and the measured amount of steps required for moving the threaded rod 14 downwards to the exact starting position defines the actual backlash of the piston. This actual backlash is automatically forwarded to the operating system of the pipette to be taken into account during different pipetting operations.

In some cases, there might also be need to take into account the possible hysteresis or other possible measurement inaccuracies of the device for measuring the actual backlash of the piston. This can be implemented so that the measurement of the backlash is carried out both for upwards movement and downwards movement of the piston. Since the mechanical backlash is generally constant for both directions, the difference of the measured backlash values in different piston movement directions gives the actual value of these measurement inaccuracies. For taking account, the effect of these measurement inaccuracies, the measured inaccuracy may be used as such to compensate the movement of the piston, or average value of the measured backlash values from different movement directions may be used for the set backlash value.

Figure 2:
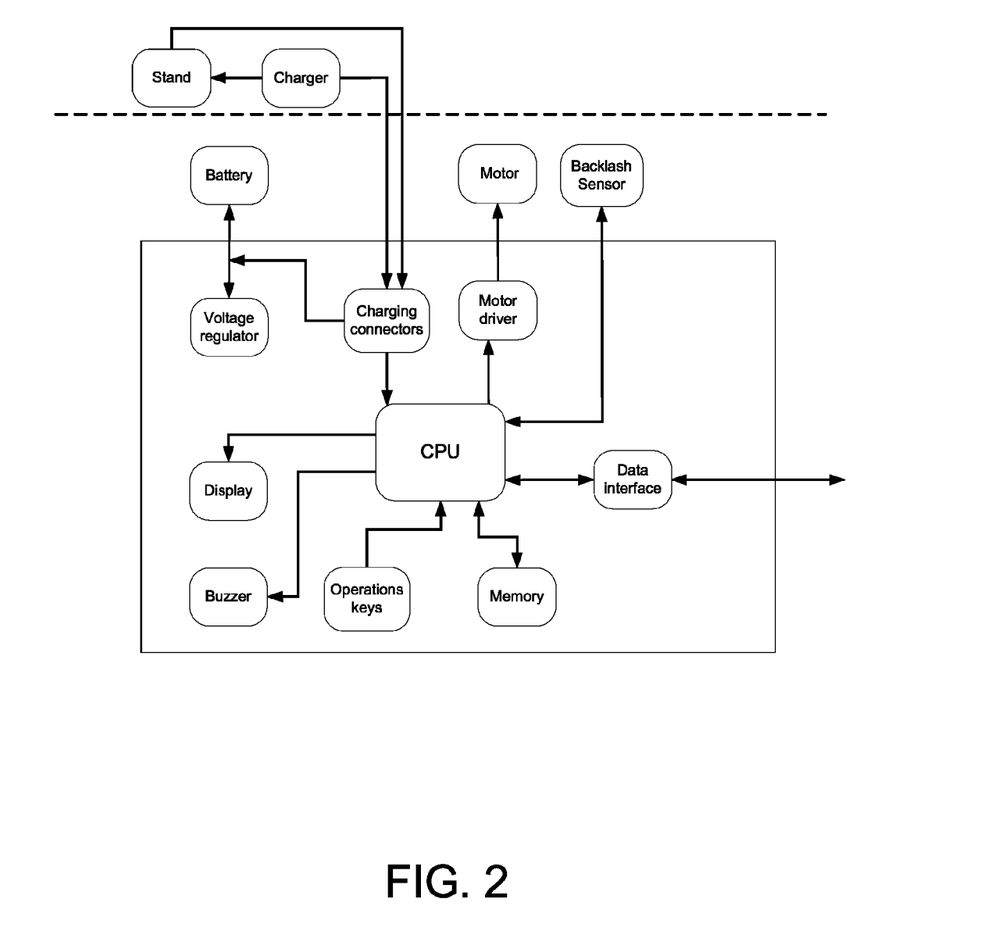
FIG. 2 shows schematically a functional diagram of an electronic pipette according to the present invention.

FIG. 2 shows schematically an example of a functional diagram of an electronic pipette, like the pipette 1 of FIG. 1. The operations of the pipette are controlled with a central processing unit (CPU), which is equipped with memory for storing pre-programmed operations and functions. The user gives commands to the CPU through operation keys and with help of a display of the pipette. The CPU is supplied with operating power by a battery and a voltage regulator, which can be recharged with a charger through charging connections when the pipette is placed in its stand. The CPU of the pipette can also be connected to external databases through data interface. The CPU receives information from a backlash sensor of the pipette and calculates the backlash value to be used in the pipetting operations and then compensates the actual backlash of the piston movement. In accordance with instructions received from the user through the operation keys, the CPU controls the motor of the pipette through a motor driver. The dashed line on FIG. 3 presents boundary surface between the pipette itself and the stand of the pipette in which the pipette is placed when not in use.

Figure 3A:
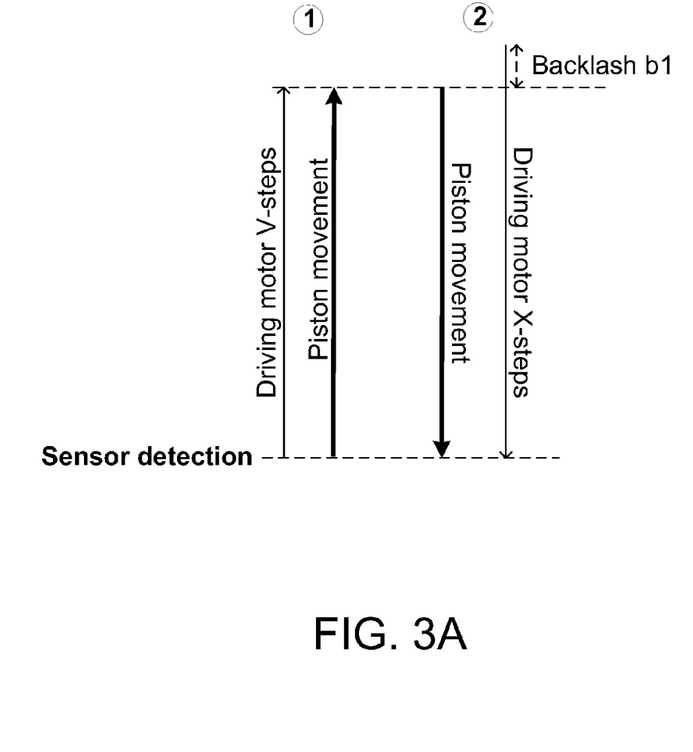
FIGS. 3A and 3B show schematically an example of the principle of the present invention for measuring the backlash of a piston in an electronic pipette.
Figure 3B:
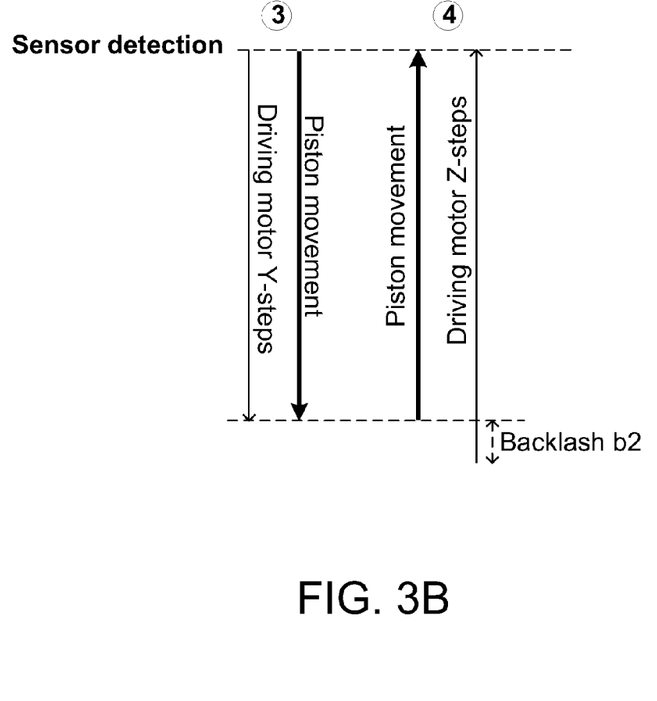

FIGS. 3A and 3B show schematically an example of the principle of the present invention for measuring the backlash of a piston in an electronic pipette. In FIG. 3A, the backlash affecting downward movement of a piston of an electronic pipette is defined and measured, i.e., the backlash affecting dispensing pipetting actions. In FIG. 3B the backlash affecting upwards movement of a piston of an electronic pipette in defined and measured, i.e., the backlash affecting aspiration pipetting action.

Before the definition and measurement of backlash is started, the position of the piston is precisely defined with a sensor. Next, as shown in FIG. 3A, the piston is moved upwards by controlling the motor to drive the piston upwards for set amount of steps (V-steps). After the piston is moved to its upward position, the motor is controlled to drive the piston downwards back to the starting position defined by the sensor, and the required steps of motor are counted (X-steps). Backlash b1 for downward movement of the piston is then defined by subtracting V-steps from X-steps.

For defining and measuring backlash of the piston for upward movement, as shown in FIG. 3B, first the position of the piston is precisely defined with the sensor. Then the piston is moved downwards by controlling the motor to drive the piston downwards for set amount of steps (Y-steps). After the piston is moved to its downward position, the motor is controlled to drive the piston upwards back to the starting position defined by the sensor, and the required steps of motor are counted (Z-steps). Backlash b2 for upward movement of the piston is then defined by subtracting Y-steps from Z-steps.

As can be seen from FIGS. 3A and 3B, when the direction of the movement of the piston is changed, the motor will first cover the length of the backlash before the piston itself starts to move. Further, this definition and measurement of backlash is advantageously implemented for both directions of movement each time the backlash is defined. If the measured backlashes b1 and b2 are not equal, mean value of these two measured backlash values can be used.

Figure 4:
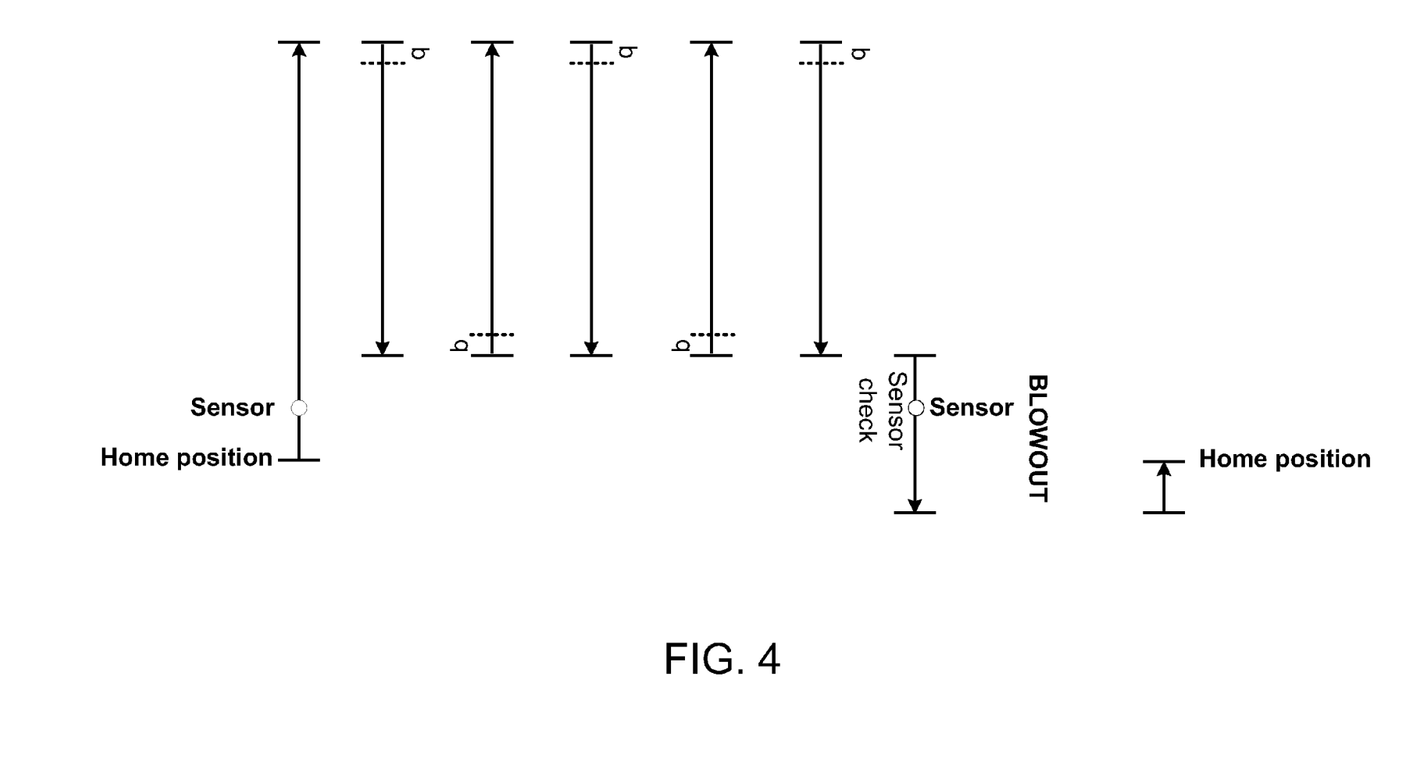
FIG. 4 shows schematically an example of motor driving of a piston of an electronic pipette according to the present invention during repetitive pipetting.

FIG. 4 shows schematically an example of motor driving of a piston of an electronic pipette according to the invention during repetitive pipetting. Repetitive pipetting technique is a commonly used technique which offers rapid and simple procedure for repeated delivery of the same liquid volume.

In repetitive pipetting technique, liquid volume larger than the required liquid volume to be dispensed during the repetition is aspired into the pipette. Then the required amount of repetitions is carried out, and finally any remaining liquid is removed from the pipette through blowout phase. After blowout phase, the motor moves the piston back at home position for any further pipetting actions.

In the example of FIG. 4, the motor moving the piston of the pipette is driven the measured backlash value extra, so that the piston itself will move only the user defined value and aspirate and dispense exactly the required liquid volume.

In FIG. 4, the "Sensor" position and the relating "Sensor check" are used to check and properly position the piston to its home position.

Figure 5:
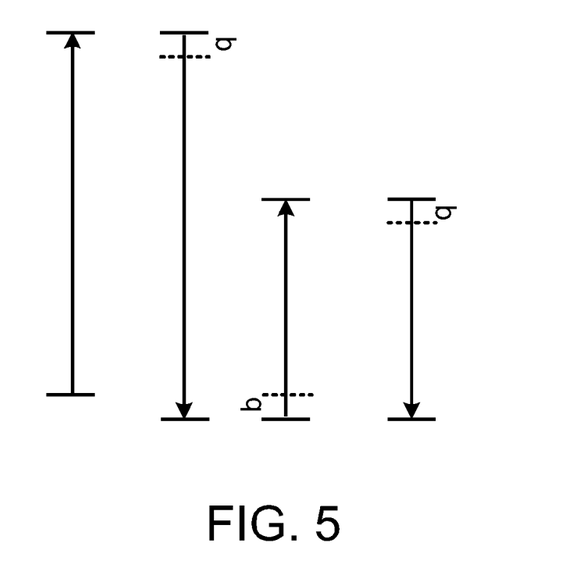
FIG. 5 shows schematically an example of motor driving of a piston of an electronic pipette according to the present invention in manual pipetting.

FIG. 5 shows schematically an example of motor driving of a piston of an electronic pipette according to the present invention in manual pipetting. The manual pipetting technique in an electronic pipette can be used in different applications. It can be used, for example, to measure the amount of remaining liquid in reservoir. In manual pipetting liquid is aspired as long as the pipetting trigger or operating switch is kept pressed. In such use, the display of the pipette shows the amount of volume that has been aspired into the pipette tip. During manual pipetting it is generally also possible to change between aspiration and dispensing whenever needed, which requires an exact compensation of backlash.

In the example of FIG. 5, in the first aspiration phase the motor drives the piston from the start until the end without any backlash, and when the first dispensing phase is started, the motor will first drive downwards the distance of the measured backlash b, which will not actually move the piston itself and the aspired liquid volume will not change at the display of the pipette. When actual movement of the piston is obtained with motor driving, the displayed volume will start to change accordingly. In the next aspiration phase, which is after dispensing of the total liquid volume from the pipette tip as can be seen from the FIG. 5, the motor will first drive the distance of the measured backlash b during which the displayed volume remains zero, and only after the actual movement of the piston is obtained will the displayed liquid volume start to increase accordingly. And similarly, when the second dispensing phase is started, the motor drives first the measured backlash b before the actual movement of the piston is achieved and before the displayed volume will change accordingly.

Figure 6:
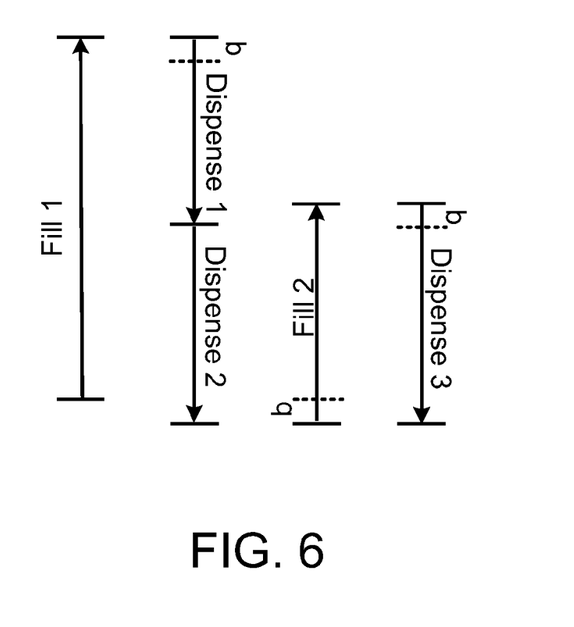
FIG. 6 shows schematically an example of motor driving of a piston of an electronic pipette according to the present invention in step based pipetting.

FIG. 6 shows schematically an example of motor driving of a piston of an electronic pipette according to the present invention in step based pipetting. In step based pipetting technique, each pipetting step is generally input separately by the user in the sequence in which these pipetting steps will be performed. This allows the user to make individual and even complicated pipetting sequences. Thus, a step based pipetting sequence can contain several phases where piston movement direction is changed and each piston movement direction change requires an exact compensation of backlash.

In the example of FIG. 6, the first fill 1 is implemented with motor driving the piston with any backlash, since locating the piston at the starting home position also removes the backlash for aspiration. After fill 1, the pipette tip is emptied with two dispensing operations dispense 1 and dispense 2, wherein during dispense 1 the measured backlash b is removed by driving the motor defined amount before actual movement of the piston together with dispensing action is obtained. In fill 2 and dispense 3 phases the measured backlash b is similarly removed with motor drive before actual movement of the piston is obtained and thus also the actual aspiration or dispensing function.

In all three pipetting techniques discusses above, the dispensing accuracy is dependent on how precisely the exact backlash value of a given pipette is known and then compensated. The present invention provides a solution for determining the actual backlash value with a measurement system integrated in the electronic pipette itself and by that also enables the renewal of the measurement and compensation throughout the life cycle of the pipette.

The specific exemplifying embodiments of the present invention shown in figures and discussed above should not be construed as limiting. A person skilled in the art can amend and modify the exemplary embodiments described above in many evident ways within scope of attached claims. Thus, the present invention is not limited merely to the embodiments described above.

What is claimed is:

1. A method for controlling an electronic pipette, which pipette comprises:
   a piston actuated in a cylinder by a motor, which motor is controlled with a control system, which control system is controlled through a user interface for operating the pipette,
   wherein an actual backlash affecting movement of the piston of the electronic pipette is measured with a system located in the pipette, the measured backlash value is forwarded to the control system of the electronic pipette, and the movement of the piston is adjusted by the control system based on the measured backlash value.

2. The method according to claim 1, wherein the backlash is measured by defining the actual position of the piston in a first position, then moving the piston a set distance to a second position, then returning the piston to the first position and measuring the returning distance, and then comparing the set distance from the first position to the second position and the measured distance from the second position to the first position.

3. A method according to claim 1, wherein the backlash is measured in both movement directions of the piston.

4. A method according to claim 3, wherein an average value of the measured backlash values from different movement directions is used as the measured backlash value for adjustment of the movement of the piston.

5. A method according to claim 1, wherein the backlash measurement is carried out each time the electronic pipette is powered up or during calibration process of the electronic pipette.

6. A method according to claim 1, wherein the backlash measurement is carried out by the electronic pipette which is a handheld entity.

7. A method according to claim 1, wherein the backlash measurement is carried out during repetitive pipetting, in manual pipetting or in step based pipetting.

8. An electronic pipette, comprising:
   a piston actuated in a cylinder by a motor,
   a control system for carrying out pipetting operations, and
   a user interface for operating the pipette,
   wherein the pipette further comprises a device configured to measure actual backlash affecting movement of the piston of the electronic pipette, and
   wherein the control system is configured to adjust the movement of the piston based on the measured backlash value.

9. The electronic pipette according to claim 8, wherein the device for measuring the actual backlash comprises an optical fork sensor.

10. The electronic pipette according to claim 8, wherein the device for measuring the actual backlash is attached to a fixed structure of the pipette, to the piston of the pipette or to a part moving with the piston.

11. The electronic pipette according to claim 8, wherein the device for measuring the actual backlash comprises one or more parts attached to the fixed structure of the pipette and one or more parts attached to the piston of the pipette or to a part moving with the piston.

12. The electronic pipette according to claim 8, wherein the electronic pipette is a handheld entity.

* * * * *